(12) United States Patent
Gao et al.

(10) Patent No.: US 7,940,043 B2
(45) Date of Patent: May 10, 2011

(54) NMR METHOD OF DETECTING PRECIPITANTS IN A HYDROCARBON STREAM

(75) Inventors: Shuqiang Gao, Pearland, TX (US); Waylon V. House, Lubbock, TX (US); Walter Chapman, Houston, TX (US)

(73) Assignees: William Marsh Rice University, Houston, TX (US); Texas Tech University, Lubbock, TX (US)

( * ) Notice: Subject to any disclaimer, the term of this patent is extended or adjusted under 35 U.S.C. 154(b) by 301 days.

(21) Appl. No.: 12/281,605

(22) PCT Filed: Mar. 13, 2007

(86) PCT No.: PCT/US2007/063876
§ 371 (c)(1), (2), (4) Date: Nov. 25, 2008

(87) PCT Pub. No.: WO2007/106810
PCT Pub. Date: Sep. 20, 2007

(65) Prior Publication Data
US 2009/0256562 A1  Oct. 15, 2009

(51) Int. Cl.
*G01V 3/00* (2006.01)
(52) U.S. Cl. .......................... 324/303; 324/300
(58) Field of Classification Search ............... 324/300, 324/303; 166/66, 53, 303, 75, 272; 436/50
See application file for complete search history.

(56) References Cited

U.S. PATENT DOCUMENTS

| | | | |
|---|---|---|---|
| 4,028,060 A * | 6/1977 | Godsey | 436/32 |
| 5,446,681 A * | 8/1995 | Gethner et al. | 702/27 |
| 5,712,165 A | 1/1998 | Alvarez et al. | |
| 5,766,952 A | 6/1998 | Mann et al. | |
| 6,000,468 A * | 12/1999 | Pringle | 166/53 |
| 6,292,756 B1 * | 9/2001 | Lievois et al. | 702/50 |
| 6,346,813 B1 * | 2/2002 | Kleinberg | 324/303 |
| 6,773,921 B1 * | 8/2004 | Schabron et al. | 436/29 |
| 6,891,369 B2 * | 5/2005 | Hurlimann et al. | 324/303 |
| 2007/0224692 A1 * | 9/2007 | Agar et al. | 436/150 |
| 2009/0264598 A1 * | 10/2009 | Bittner et al. | 525/231 |
| 2009/0286295 A1 * | 11/2009 | Medoff et al. | 435/162 |

OTHER PUBLICATIONS

Foreign communication from priority application, International Search Report and Written Opinion, PCT/US07/63876, Oct. 26, 2007, 7 pages.

* cited by examiner

*Primary Examiner* — Brij B Shrivastav
(74) *Attorney, Agent, or Firm* — Conley Rose, P.C.; Rodney B. Carroll

(57) ABSTRACT

A method for detecting the presence of precipitants in a hydrocarbon stream, the method comprising introducing at least a portion of the hydrocarbon stream into a measurement chamber of an NMR measuring device, assaying the fluids in the chamber with proton nuclear magnetic resonance to obtain NMR signals, and processing the NMR signals to detect the formation of precipitants in the hydrocarbon stream. The method may be carried out at first and second locations, and NMR signals obtained at the two locations compared to detect precipitation of precipitant between the two locations. A method of monitoring the water content of a hydrocarbon stream in a flowline comprising introducing at least a portion of the hydrocarbon stream into an NMR measuring device, measuring a baseline NMR water signal of the hydrocarbon stream and comparing subsequent NMR water signals with the baseline NMR water signal to detect changes in the water content of the hydrocarbon stream.

20 Claims, 9 Drawing Sheets

NMR METHOD OF DETECTING PRECIPITANTS IN A HYDROCARBON STREAM

STATEMENT REGARDING FEDERALLY SPONSORED RESEARCH OR DEVELOPMENT

Not applicable.

BACKGROUND

1. Field of the Invention

The present disclosure relates generally to NMR methods of detecting precipitants in a hydrocarbon stream. More particularly, this disclosure relates to the use of NMR spectroscopy or NMR relaxometry for detecting or predicting formation of solids in a hydrocarbon stream.

2. Background of the Invention

Gas hydrates are ice-like structures in which water molecules, under pressure, form structures composed of clathrate hydrate cages which are nano-scale polyhedral cages surrounding gas molecule "guests" such as methane and ethane. Rarely encountered in everyday life, hydrates occur in abundance under sea floor and permafrost environments where (P, T) conditions ensure hydrate stability. Natural gas trapped in these deposits represents a potential source of energy many times known natural gas reserves. Hydrates can form as well in undersea piping and above ground pipelines where they pose a major problem for gas/oil producers.

Hydrate plugs are often formed during oil production, due to the presence of water and light hydrocarbons such as methane at low temperatures and high pressures. Hydrate can be formed by nitrogen, carbon dioxide, hydrogen sulfide, methane, ethane, propane, iso-butane, n-butane, and some branched or cyclic C5-C8 hydrocarbons. When natural gases such as methane come into contact with water at high pressure and low temperature, the formation of gas hydrates can lead to problems with flow assurance, i.e. the assurance of unrestricted flow of fluids through pipelines. Formation of hydrate can plug natural gas pipelines and reduce or inhibit flow. Hydrate plugs can cause serious safety issues as well as problems with deep-water flow assurance in oil and gas flow lines.

To prevent hydrate plugging, chemical hydrate inhibitors are often added into the pipelines. Additionally, thermal insulations can be installed to prevent heat loss so that temperature does not drop to the point where conditions are favorable to hydrate formation. The use of hydrate inhibitors is an imprecise science and is an industry exceeding $500 million dollars annually. Dose rates of hydrate inhibitors and thermal insulation designs are based on the expected pipeline conditions relative to the hydrate phase diagram. Therefore, accurate phase diagrams are essential to safety and economic considerations. Equally important are hydrate formation and dissociation kinetics, key factors in hydrate management. Unfortunately, current models for predicting hydrate phase behavior show considerable discrepancy with experimental data for black oil systems. The differences can be as much as a 5-6 degree temperature change, which will either invoke unnecessary expense or put the operation at great risk. New experimental data is needed to test and tune phase behavior models. However, hydrate phase behavior in black oil, particularly with emulsions, is poorly understood due to the associated experimental difficulties. No kinetic data on gas hydrates in black oil has yet been reported.

Since hydrate cannot be visually observed in black oil, some methods rely on measuring gas pressure and temperature changes in order to predict when conditions are ripe for hydrate formation. One method is to monitor the pressure changes in a closed volume system. In this method, natural gas, black oil, and gas are charged to a high pressure cell. The pressure is monitored as the closed system is ramped in temperature. Because the gases have to transport through the liquid oil and water phases, some means of mechanical stirring is often employed to facilitate the gas mass transfer. Pressure drops dramatically upon hydrate formation because hydrate formation consumes large quantities of gas. After hydrate formation, the temperature is raised to dissociate the hydrate. As hydrate dissociates, gas is evolved and the pressure increases significantly. The transition point that indicates complete hydrate dissociation, (normally where pressure and temperature return to the original P, T curve before hydrate formation), is identified as the hydrate thermodynamic point.

Because gases have to diffuse through the liquid phase for hydrate behavior to create pressure responses, the complication of gas mass transfer is involved and hydrate behavior is only indirectly observed. Due to the slow diffusion of gases in black oil, pressure responses are often delayed which leads to subsequent delay in hydrate formation prediction. It is difficult to determine the correct hydrate onset point since the determination of ripe conditions does not always mean hydrates will immediately form. This pressure monitoring technique encounters difficulties when the oil phase is too viscous, the amount of water is too small, or the gas phase is absent.

Another problem encountered in pressure and temperature change based monitoring systems is the inability to acquire correct hydrate equilibrium points in black oil. In systems which have the ability to form multi-hydrates, such as natural gas and black oil, the thermodynamic point of hydrates occurs at equilibrium when the last hydrate crystal dissociates. Because the dissociation of several small hydrate crystals can be easily missed by simply tracking the gas pressure change, hydrate crystals can remain in black oil even though the pressure change indicates a complete dissociation of hydrate.

Finally, in oil and gas production, occasionally several small hydrates may form individually rather than in large clumps. When this occurs, the accuracy in predicting the amount of hydrate via traditional methods is compromised.

Accordingly, an ongoing need exists for a method to detect and/or predict precipitant formation in a hydrocarbon stream enabling a more efficient and substantially less costly use of precipitation inhibitors.

SUMMARY

Disclosed herein are methods for detecting the presence of precipitants in a hydrocarbon stream. The presence of precipitants may be detected by introducing at least a portion of the hydrocarbon stream into a measurement chamber of an NMR measuring device, assaying the fluids in the chamber with proton nuclear magnetic resonance to obtain NMR signals, and processing the NMR signals to detect the formation of precipitants in the hydrocarbon stream.

NMR spectroscopy or NMR relaxometry may be used to assay the fluids in the chamber. The NMR signals may be monitored to detect changes in the liquid water content over time which can be correlated with hydrate formation. The methods may be used to detect the formation and dissociation of hydrates in an emulsion by monitoring the water peaks using in situ proton nuclear magnetic resonance spectroscopy or relaxometry. The method may be used to monitor the NMR signals to detect changes in the liquid water content substantially in real time.

NMR spectroscopy may be used to assay the fluids in the chamber and the liquid water peaks of the measured frequency spectra may be monitored to detect changes in liquid water content. A baseline NMR liquid water signal for the hydrocarbon stream may be measured, an operating range having a low NMR liquid water signal and a high NMR liquid water signal may be defined, and a response may be signaled if a subsequently measured NMR liquid water signal falls outside the predetermined operating range.

NMR relaxometry may be used to assay the fluids in the chamber. NMR relaxometry may comprise measuring a baseline $T_2$ relaxation distribution of the hydrocarbon stream and subsequently measuring the $T_2$ relaxation distribution of the hydrocarbon stream over time, and processing the NMR signals obtained to detect the formation of precipitants in the hydrocarbon stream may comprise monitoring subsequently measured $T_2$ distributions of the hydrocarbon stream to detect a shift in the $T_2$ distribution from baseline indicating the formation of solid precipitant. NMR relaxometry may be used to detect a precipitant selected from, but not limited to, hydrates, asphaltenes, paraffins, and combinations thereof.

The method may be implemented in a device connected to a transport pipeline. The method may comprise introducing at least a portion of the hydrocarbon stream into a measurement chamber of an NMR measuring device by pulling a slipstream from the transport pipeline.

A method of monitoring the water content of a hydrocarbon stream in a flowline comprises introducing at least a portion of the hydrocarbon stream into an NMR measuring device, measuring a baseline NMR water signal of the hydrocarbon stream and comparing subsequent NMR water signals with the baseline NMR water signal to detect changes in the water content of the hydrocarbon stream. A response may be signaled if the water content of the hydrocarbon stream changes by more than 5% from the baseline water content. The monitoring of the NMR signals to detect changes in the liquid water content may occur substantially in real time.

A method of analyzing a hydrocarbon stream comprises obtaining NMR signals at a first location, obtaining NMR signals at a second location downstream of the first location, and comparing the NMR signals obtained at each location to detect precipitation of precipitant between the two locations. Comparing the NMR signals obtained at each location to detect precipitation of precipitant between the two locations may comprise monitoring relaxation distribution, frequency spectra, or both at the first and second locations and comparing the relaxation distribution, frequency spectra, or both at the first and second locations to detect changes in the liquid water content of the hydrocarbon stream and correlating changes in liquid water content with precipitant formation. The change in liquid water content between the two locations may be correlated with hydrate formation. The change in liquid water content between the two locations may be correlated with ice formation. Assaying the fluids in the chamber at each location with proton nuclear magnetic resonance may comprise performing NMR relaxometry to determine the $T_2$ relaxation distribution, measuring a baseline $T_2$ relaxation distribution, and correlating a shift of subsequently measured $T_2$ relaxation distribution from the baseline $T_2$ relaxation distribution with precipitant formation. The areas under the $T_2$ relaxation distribution curves may be calculated to determine amount of precipitant precipitated between the two locations. The method of analyzing a hydrocarbon stream comprising carrying out the NMR method at a first location and carrying out the NMR method at a second location downstream of the first location may be used to detect a precipitant including, but not limited to, paraffins, asphaltenes, hydrates, and combinations thereof. The first and second locations may be locations along a transport pipeline.

A method for determining the hydrate thermodynamic point of a hydrocarbon stream comprises, over a range of temperatures, introducing at least a portion of the hydrocarbon stream into a measurement chamber of an NMR measuring device, assaying the fluids in the chamber with proton nuclear magnetic resonance spectroscopy to obtain NMR signals, determining the amount of hydrate present at each temperature from the liquid water peaks of the NMR frequency spectra, and determining the hydrate thermodynamic point of the hydrocarbon stream as the temperature at which the last hydrate crystal dissociates.

DETAILED DESCRIPTION OF THE INVENTION

Notation and Nomenclature

As used herein, the term relaxometry is used to refer to the study and/or measurement of relaxation variables in nuclear magnetic resonance (NMR) and magnetic resonance imaging (MRI).

Overview

Disclosed herein is a method to detect and quantify the kinetics and amount of precipitated phase, including, but not limited to, gas hydrate, asphaltene, and wax in a hydrocarbon stream utilizing nuclear magnetic resonance (NMR). The method may also be used to predict the onset of precipitation within a flowline. As further discussed hereinbelow, directly observing the proton shift/spin or relaxation time distribution in the hydrocarbon stream with NMR allows determination of variant amounts of both water and hydrocarbon in the hydrocarbon stream. By observing the water and hydrocarbon peak shifts or changes in relaxation time distribution in both static and dynamic systems, a quantified amount of precipitated phase within the system may be determined.

In embodiments of the disclosed method, NMR spectroscopy is used to detect the presence of precipitants. In embodiments, NMR spectroscopy is used to directly observe the liquid-to-solid conversion of the water component in a hydrocarbon stream. In alternative embodiments, NMR relaxometry is used to detect the presence of precipitants in a hydrocarbon stream.

The hydrocarbon stream may, for example, comprise oil, gas, and similar emulsions. The methods may be particularly useful for the oil industry where flowlines are often at low temperatures and high pressures and favor the formation of hydrates which leads to flow assurance problems. For example, in deep sea oil/gas productions, hydrocarbon streams are subjected to temperatures around 4° C. and high pressures. Upon increasing the pressure, ice formation occurs at lower temperatures, but hydrate formation occurs at higher temperatures at higher pressures. Thus, hydrate formation can be a problem in hydrocarbon streams from deep-sea productions.

The disclosed method for detecting the presence of precipitants in a hydrocarbon stream comprises introducing at least a portion of the hydrocarbon stream into a measurement chamber of a proton nuclear magnetic resonance (NMR) measuring device, assaying the fluids in the chamber with proton NMR to obtain NMR signals, and processing the NMR signals obtained to detect the formation of precipitants in the hydrocarbon stream.

In embodiments, assaying the fluids in the chamber comprises performing NMR spectroscopy on the fluids in the chamber. In embodiments, monitoring the NMR signals to detect the formation of precipitants in the hydrocarbon stream comprises monitoring the changes in the NMR spectra with time.

Figure 1:
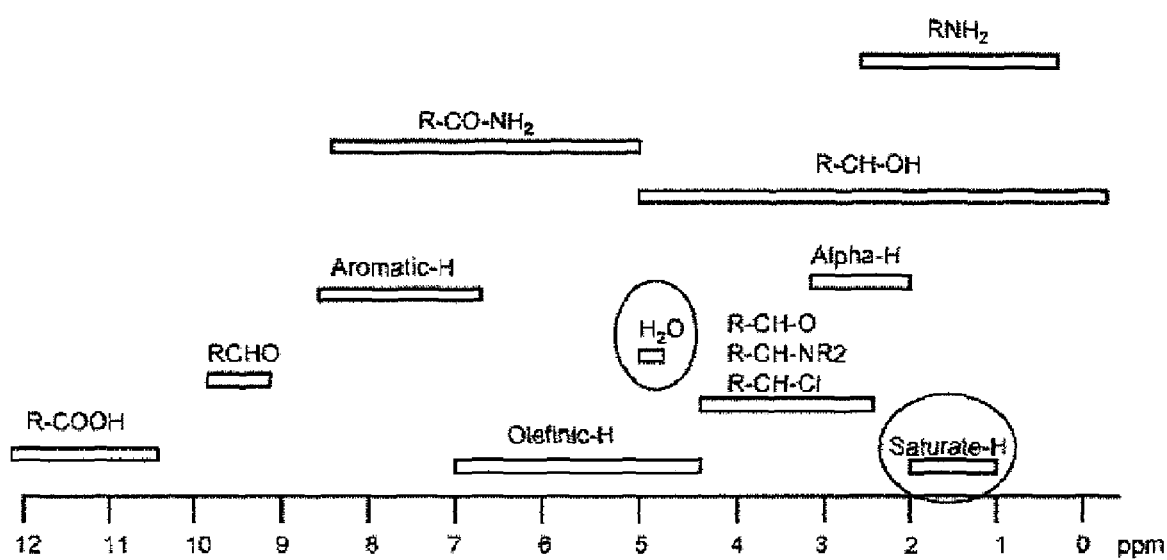
FIG. 1 is a schematic of proton NMR chemical shifts for common functional groups.

In a proton NMR spectrum, different hydrogen functional groups have different chemical shifts. The chemical shifts of water and saturated hydrocarbons, the dominant components in black oil and natural gas, are about 3 ppm apart, as shown in FIG. 1, which is a schematic of proton NMR chemical shifts for common functional groups. As further described in Example 1 hereinbelow, oil and gas components form a single broad peak in the NMR frequency spectrum. As discussed further in Example 1 and as shown in the NMR frequency spectra of FIG. 2, with high magnetic fields of adequate homogeneity, the water peak can be distinguished from oil/gas peaks in the NMR frequency spectra, the peaks being about 3 ppm (255 Hz) apart, as expected from FIG. 1.

Because the free induction decay of water in gas hydrates at suitable conditions is short and the spectral line of gas hydrates is broad, gas hydrates cease to contribute to the liquid water peak, and the water peak consequently decreases as hydrates form. Water becomes essentially invisible to liquid state NMR as it becomes immobile, due to hydrate or ice formation. By tracking the water peak area of the NMR spectra, therefore, the degree of hydrate formation and dissociation in oil and gas production may be monitored, and, at lower temperatures, the formation of ice. This method allows the real-time detection (the measurement takes only seconds to accomplish) and facile quantification of hydrate formation and dissociation from changes in water peak area, rather than traditional (P, T) ramping techniques that rely upon pressure responses (and assume that pressure changes represent formation or dissociation of hydrates rather than simply changes in solubility).

Changes in water NMR peak height signal hydrate formation or dissociation, and water peak area may be linearly correlated with the amount of water present in the sample. By measuring the change of peak area, the amount of water in the emulsion that has formed gas hydrates (and/or ice) may be calculated. In embodiments, the water peak area is determined with an error of less than ±1%. In embodiments, assaying the fluids in the chamber with proton nuclear magnetic resonance comprises performing NMR spectroscopy and processing the NMR signals comprises monitoring the spectra to detect changes in the liquid water content over time which can be correlated with hydrate formation.

In some embodiments of the disclosed method, assaying the fluids in the chamber comprises performing NMR relaxometry on the fluids in the chamber. As known to those of skill in the art, NMR relaxometry techniques, including, without limitation, measuring NMR spin-lattice relaxation time ($T_1$) and spin-spin relaxation time ($T_2$), have been shown to be powerful techniques for studying micro-dynamic behavior of liquids and therefore of providing local molecular level structural information surrounding the NMR responsive guest molecules. MRI non-invasively and accurately captures hydrate formation and dissociation patterns, as further discussed in Example 2.

The spin-lattice relaxation time, $T_1$, is used to characterize the rate at which equilibrium is established in bulk magnetization. The spin-spin (or transverse) relaxation time constant, $T_2$, is an expression of the relaxation due to non-homogeneities in the local magnetic field over the sensing volume. Spin-spin coupling is relevant in heavy oil components, such as asphaltenes, resins, etc.

In embodiments, monitoring the NMR signals to detect the formation of precipitants in the hydrocarbon stream comprises monitoring the changes in the $T_2$ distribution of at least one component of the hydrocarbon stream with time. Examples of detectable precipitants include, without limitation, asphaltenes, paraffins, hydrates, ice, and combinations thereof.

$T_1$ and $T_2$ measurements are useful for studying the growth of supra-molecular species in solution or suspension. As discussed further in Example 3, upon formation of a precipitant, such as, for example, asphaltene, the $T_2$ distribution will shift downward indicating the formation of larger molecules. Asphaltene precipitates as a result of pressure drop, turbulent flow, acids, solution carbon dioxide, and other conditions that break the stability of asphaltic dispersion. Particularly, many black oils are known to exhibit the agglomeration of asphaltene molecules and subsequent asphaltene flocculation when subjected to $CO_2$ injection, a procedure commonly used in enhanced oil production. In embodiments, the hydrocarbon stream is a produced oil stream from a $CO_2$ injection process and the method is used to detect the presence of asphaltene precipitant by monitoring shifts in the $T_2$ distribution with time.

In some embodiments, a baseline $T_2$ distribution of the hydrocarbon stream is measured, and subsequent measurements of the $T_2$ relaxation distribution are compared to baseline, a downward shift in $T_2$ relaxation distribution being correlated with the formation of solid precipitant.

In embodiments, NMR $T_2$ distribution measurements are used for monitoring hydrate formation and dissociation. The $T_2$ distribution of guest molecules in clathrate cages can be determined along with the $T_2$ distribution of hydrocarbon molecules from within a coexisting liquid phase. Information on hydrate kinetics may be obtained by the disclosed method. The area under the $T_2$ distribution of the hydrate phase represents the population of the enclathrated hydrocarbon molecules. In embodiments, low-field NMR $T_2$ distribution measurement is used to detect precipitant formation. In embodiments, the method is used for the determination of hydrate kinetic data.

In embodiments, a baseline NMR liquid water signal is determined for the hydrocarbon stream and an operating range having a low NMR liquid water signal and a high NMR liquid water signal is determined. In embodiments, the method further comprises signaling a response when the measured NMR liquid water signal falls outside the predetermined operating range. The NMR signals may be monitored to detect changes in liquid water content substantially in real time. A suitable response may comprise setting off an alarm. In some embodiments, the response may comprise initiating a corrective action which may be any action that returns the liquid water signal to within the predetermined operating range. Without limitation, a suitable corrective action may comprise injecting a precipitation inhibitor (e.g. a hydrate inhibitor) into the hydrocarbon stream.

In embodiments, the method comprises positioning the device at a wellhead and using the method in a feedback control for determining the amount of hydrate inhibitor to add to the flowline. In alternative embodiments, the method is used in a feedback control loop for controlling the injection of chemical hydrate inhibitor at the wellhead. Alternatively, the method is used to determine the amount of thermal insulation to add to flow lines to prevent hydrate plugging.

The NMR measuring device comprises an NMR for obtaining NMR spectra or relaxometry data. The NMR is operatively connected to a processor which may be a computer programmed with NMR software. The processor is capable of implementing the methods disclosed herein with the NMR signals obtained from the NMR and also controls the NMR. In embodiments, the device comprises a low field relaxometer. Alternatively, the device comprises a high field spectrometer. The measurement chamber may comprise a flow through passage into which at least a portion of the hydrocarbon stream is introduced for monitoring.

In embodiments, the NMR measuring device is connected to a hydrocarbon transport pipeline. In embodiments, a slipstream is diverted from the transport pipeline and sent through the NMR measuring device for monitoring. By utilizing a slipstream, measurement of, for example, NMR spectra, may be performed online on flowing streams. In an embodiment, the method comprises automatically pulling a sample from the flowing stream via a slipstream and performing NMR monitoring on the sample. In embodiments, the slipstream is monitored substantially continuously. Alternatively, the method may comprise measuring a flowing stream without the need to capture a sample and hold it.

Also disclosed herein is a method of monitoring the water content of a hydrocarbon stream in a flowline. It is very important for operators to know real-time water production rate. The disclosed method comprises introducing at least a portion of the hydrocarbon stream into a measurement chamber of an NMR measuring device, assaying the fluids in the chamber with NMR to obtain NMR signals, and processing the NMR signals obtained to monitor the water content in the hydrocarbon stream. The processing of the NMR signals comprises measuring a baseline NMR water signal of the hydrocarbon stream and comparing subsequent NMR water signals with the baseline NMR water signal to detect changes in the water content of the hydrocarbon stream. In embodiments, the method further comprises signaling a response if the water content of the hydrocarbon stream changes by more than ±5% from the baseline water content. Alternatively, the method further comprises signaling a response if the water content of the hydrocarbon stream changes by more than ±3% from the baseline water content. Alternatively, the method further comprises signaling a response if the water content of the hydrocarbon stream changes by more than ±10% from the baseline water content. The disclosed method for monitoring the water content may be used to detect changes in the liquid water content substantially in real time. Furthermore, a decrease in the liquid water content may be correlated with precipitant formation, i.e. hydrate or ice formation. An increase in the liquid water content may indicate an undesirable influx of water into the producing stream.

Also presented herein is a method of analyzing a hydrocarbon stream comprising determining the presence of precipitant at two locations along a flowline and comparing the NMR data obtained at the two locations to detect precipitation of a precipitant between the two locations. For example, the two locations may be distinct locations along a transport pipeline. In embodiments, the NMR frequency spectra, the relaxation distribution, or both are analyzed at the two locations and the NMR frequency spectra, the relaxation distributions, or both are compared to detect changes in the liquid water content of the hydrocarbon stream between the two locations. The change in liquid water content can be correlated with precipitant (e.g., hydrate, ice) formation. In some embodiments, NMR relaxometry is performed at the two locations to monitor changes in $T_2$ distribution between the two locations. As discussed hereinabove, changes in the $T_2$ distribution between the two locations can be correlated with precipitant formation. The areas under the $T_2$ distribution curves may be used to determine the amount of precipitant precipitated. In some embodiments, $T_2$ distributions are compared between the two locations to determine the precipitation of a precipitant selected from the group consisting of asphaltenes, paraffins, hydrates, ice, and combinations thereof. The spin-spin relaxation time, $T_2$, may also be correlated with mean particle size as is known to those of skill in the art. The mean particle size at each of the two locations can be monitored and compared to detect precipitant formation.

In embodiments, the disclosed method may be used in combination with conventional pressure measurements to reveal information on the time lags inherent in pressure measurements and provide data on gas migration.

In addition, the disclosed methods may be used to dynamically and accurately measure hydrate nucleation and/or dissociation, hydrate concentration within a system, and rate of hydrate formation/dissociation. The method may be used to provide accurate hydrate thermodynamic and kinetic information. For example, a method for determining the hydrate thermodynamic point of a hydrocarbon stream may comprise: over a range of temperatures, introducing at least a portion of the hydrocarbon stream into a measurement chamber of an NMR measuring device, assaying the fluids in the chamber with proton NMR spectroscopy to obtain NMR signals, determining the amount of hydrate present at each temperature from the liquid water peaks of the NMR frequency spectra, and determining the hydrate thermodynamic point of the hydrocarbon stream as the temperature at which the last hydrate crystal dissociates (see Example 1). The method of determining the hydrate thermodynamic point of a hydrocarbon stream may be used to maintain flow assurance of a hydrocarbon stream along a transport pipeline by determining the hydrate thermodynamic point of the hydrocarbon stream and maintaining the temperature of the transported hydrocarbon stream above the hydrate thermodynamic point.

Results (see Example 1) illustrate that emulsion formation depresses the hydrate thermodynamic point in oil and gas production. As found in Example 1, methane hydrate dissociates over a range of temperature in oil and gas production, theorized to be because the emulsion size is not uniform. Emulsion formation has a great impact on hydrate phase behavior in oil and gas production. Even though emulsion formation results in higher viscosity, it can significantly alleviate hydrate risk during oil production. As shown in Example 1, hydrate onset in an emulsion may not cause large-scale hydrate formation. Without wishing to be limited by theory, the absence of large-scale hydrate formation upon hydrate onset may be attributed to two causes. Firstly, most water drops are fairly independent of each other. Hydrate nuclei may not be shared between water droplets. Secondly, smaller water droplets exhibit lower hydrate equilibrium temperatures. The sub-cooling that causes larger droplets to form hydrate may not be enough to cause the smaller droplets to hydrate. Consequently, a large amount of water remains in liquid state after initial hydrate formation.

The disclosed method may be used to quantify the relationship between emulsion size and hydrate phase boundary, the hydrate kinetics and accurate hydrate equilibrium data in oil and gas at different water cuts and be used in hydrate management of hydrocarbon streams.

The methods of the present disclosure may further comprise performing NMR diffusivity measurements. The NMR diffusivity data may be used to calculate the viscosity of the hydrocarbon stream. NMR diffusivity measurements may be performed in any manner known to one of skill in the art.

EXAMPLES

Example 1

Gas Hydrate Behavior in Black Oil

Figure 3:
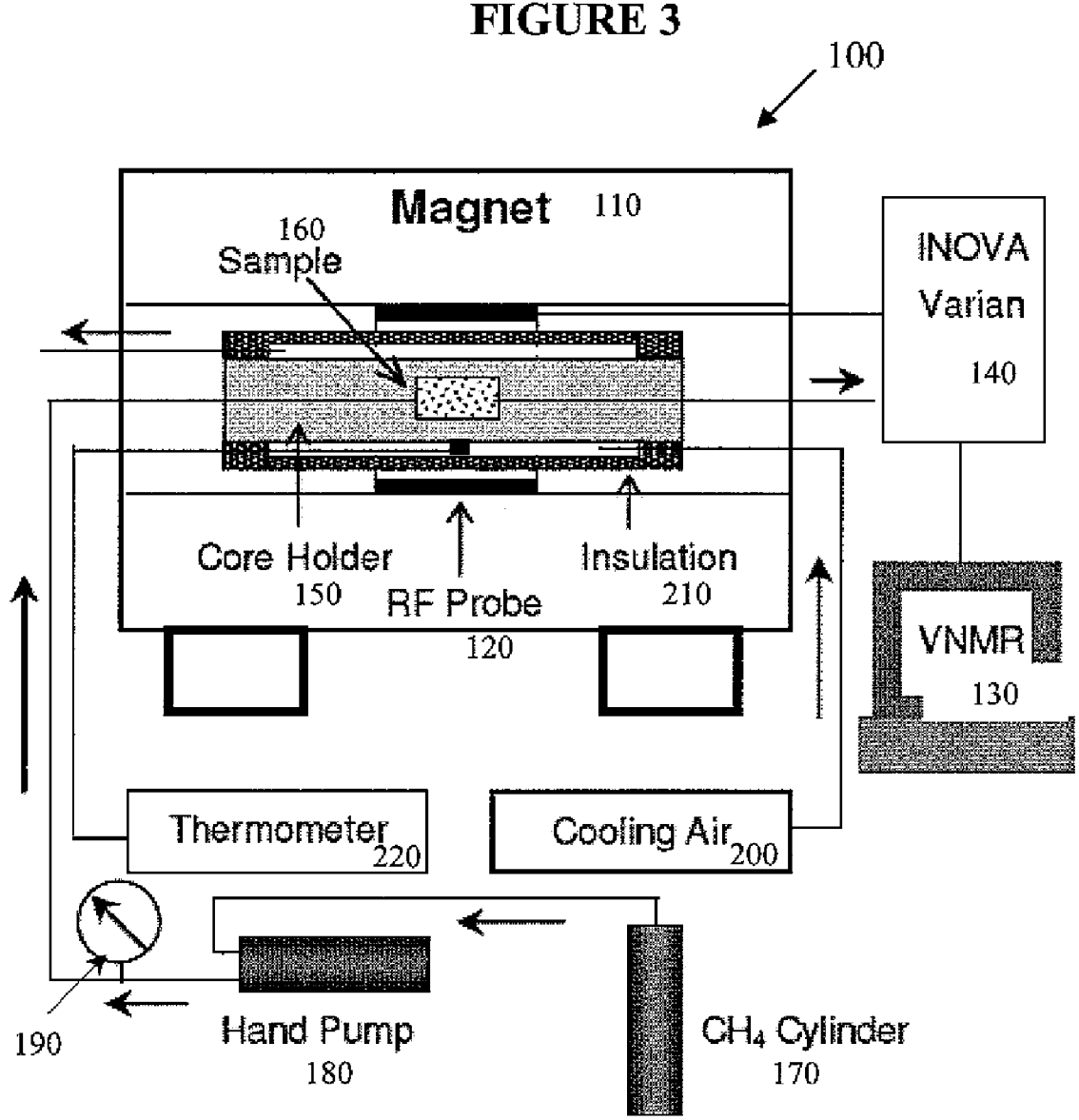
FIG. 3 is a schematic of an experimental setup for NMR spectroscopy measurements.

Experiments were performed to study the gas hydrate behavior in black oil. The experimental scheme to detect the presence of precipitants with NMR spectroscopy 100 is depicted in FIG. 3. The magnet 110 for the NMR measurements is an 85 MHz Oxford horizontal 32 cm wide bore NMR with imaging capability. The probe 120 is a LITZ RF volume coil (with 14 cm internal diameter) from Doty Scientific, Inc. NMR data were acquired and processed using Varian VNMR software 130 and INOVA hardware system 140.

Black oil (Baker Petrolite) and pure water (Aldrich Chemical Company, Inc) were mixed at 1:1 volume ratio to make a stable water-in-oil emulsion by manual shaking. The 16 ml water-in-oil emulsion sample was contained in a Teflon® bottle. The sample 160 was placed in a core holder 150 from Temco Inc, made of strong non-metal composite material and specially designed for NMR experiments. Core holder 150 is capable of handling pressures up to 2500 psi. It has an outer diameter of 5.6 cm, enclosing sample 160 having a diameter of 2.7 cm and a height of 3.1 cm. Ultra High Purity (UHP) grade methane 170 from Airgas was used as the gas phase. A Ruska positive displacement hand-pump 180 was used to control the pressure. The maximum pressure capability of the Ruska positive displacement hand-pump is 4000 psi. The gas pressure was accurately measured by a Heise high precision dial pressure gauge 190 having a resolution of 2.5 psi.

An Air-Jet temperature controller blowing dry, cold air 200 was used to control the temperature of core holder 150. The Air-Jet temperature controller provides cold air from about −40° C. to 100° C. with ±0.1° C. stability. Styrofoam material was placed around core holder 150 for insulation 210. A LUXTRON® fluoroptic thermometer 220 was mounted onto core holder 150 to monitor system temperature. LUXTRON® fluoroptic thermometer 220 has an output resolution of ±0.1° C.

With the emulsion sample 160 inside and insulation 210 outside, core holder 150 was placed into NMR probe 120. Magnetic Resonance Imaging (MRI) techniques were utilized to ensure sample 160 was located in the center of magnet 110, the location that has the most homogenous magnetic field. The more homogeneous the magnetic field, the greater the spectral resolution and signal to noise ratio. Core holder 150 was then slowly pressurized to 2000 psi with methane 170 at room temperature. The system 100 was stabilized for one day at room temperature and 2000 psi to achieve equilibrium between gas/oil/water phases. NMR system 100 was fine-tuned to yield a spectrum in which the water was distinguishable from oil/gas peaks.

After system equilibrium was assured, temperature control was used to cool core holder 150 in steps. The temperature was held constant for over 12 hours at each step. An NMR spectrum was collected at each temperature step to detect any decrease in water peak, i.e. the indication of hydrate formation. System 100 was held at ~2° C. for two weeks before the temperature was lowered to subzero. The temperature was then further lowered until most of the water peak disappeared. The pressure was maintained at 2000 psi with Ruska hand-pump 180. After the disappearance of water peak, the temperature was slowly increased in steps. Again, the temperature was held constant for over 12 hours at each step. An NMR spectrum was collected at each temperature step to detect any increase in water peak height, i.e. the indication of hydrate dissociation. The temperature was held constant for over 12 hours at each temperature step, not only to account for the temperature lag between core holder 150 and sample 160 within, but also due to potential dissociation meta-stability associated with rapid heating.

Figure 2:
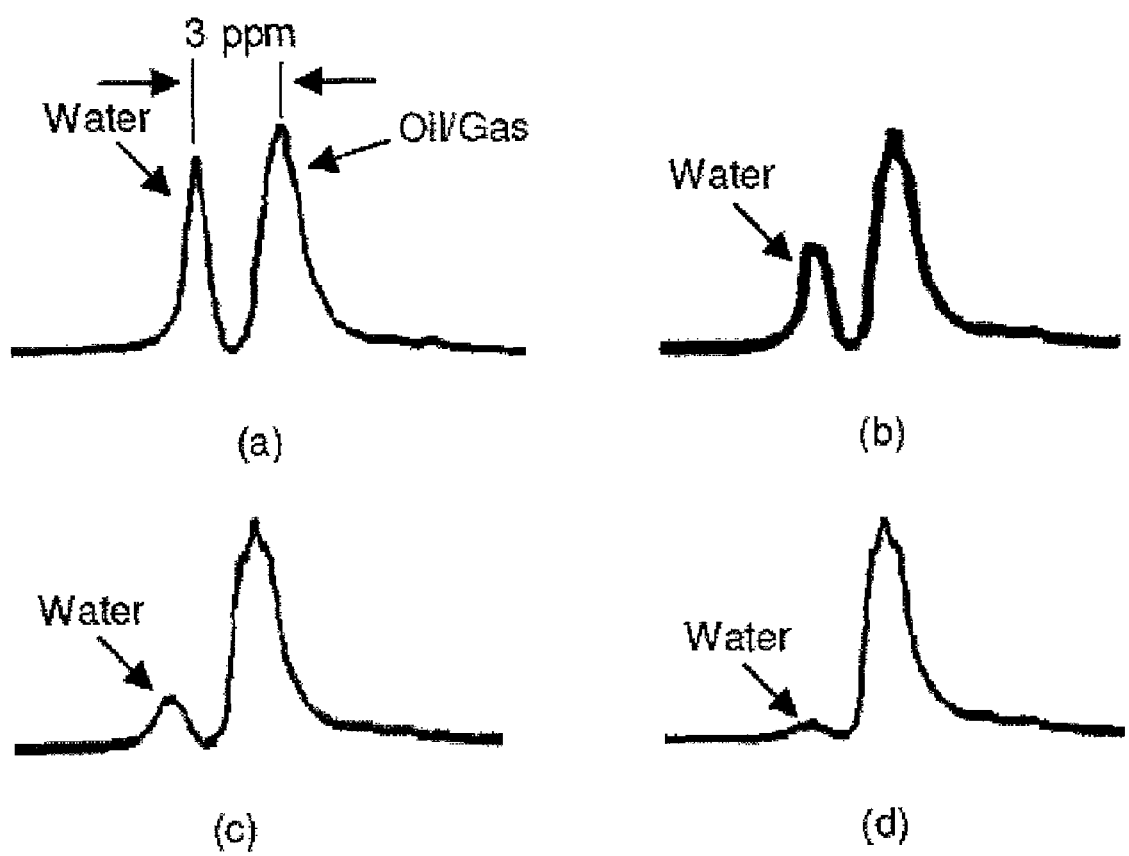
FIG. 2 shows NMR spectra at different stages of hydrate formation. From (a) to (d), as less mobile water is present, the water peak diminishes.

FIG. 2 shows the NMR spectra of the water/black oil emulsion sample with different degrees of hydrate formation. Oil and gas components form a single broad peak. The water peak and oil/gas peak are nicely separated and are about 3 ppm apart. As mentioned hereinabove, the water peak is linearly correlated with the amount of liquid water in the sample. As water turns into hydrate (and also possibly into ice when the temperature is below zero), the water peak area decreases, as shown from FIG. 2a to FIG. 2d. Peak areas were reproducible experimentally with an error of less than 1%. By measuring the change in peak area above the ice point, the amount of water in the emulsion that has formed hydrate can be calculated. From the rate of change of peak area, kinetic information can be obtained. Thus, in situ hydrate behavior in a hydrocarbon stream can be detected and accurately measured.

At 2000 psi, the predicted methane hydrate equilibrium temperature in bulk water by CSMHYD is 16.34° C. As discussed hereinabove, when water is distributed in the form of emulsion droplets, the hydrate equilibrium temperature is expected to be depressed. In this experiment, because of the variation in water droplet sizes, hydrate was expected to dissociate over a range of temperatures even though the gas was pure methane.

Figure 4:
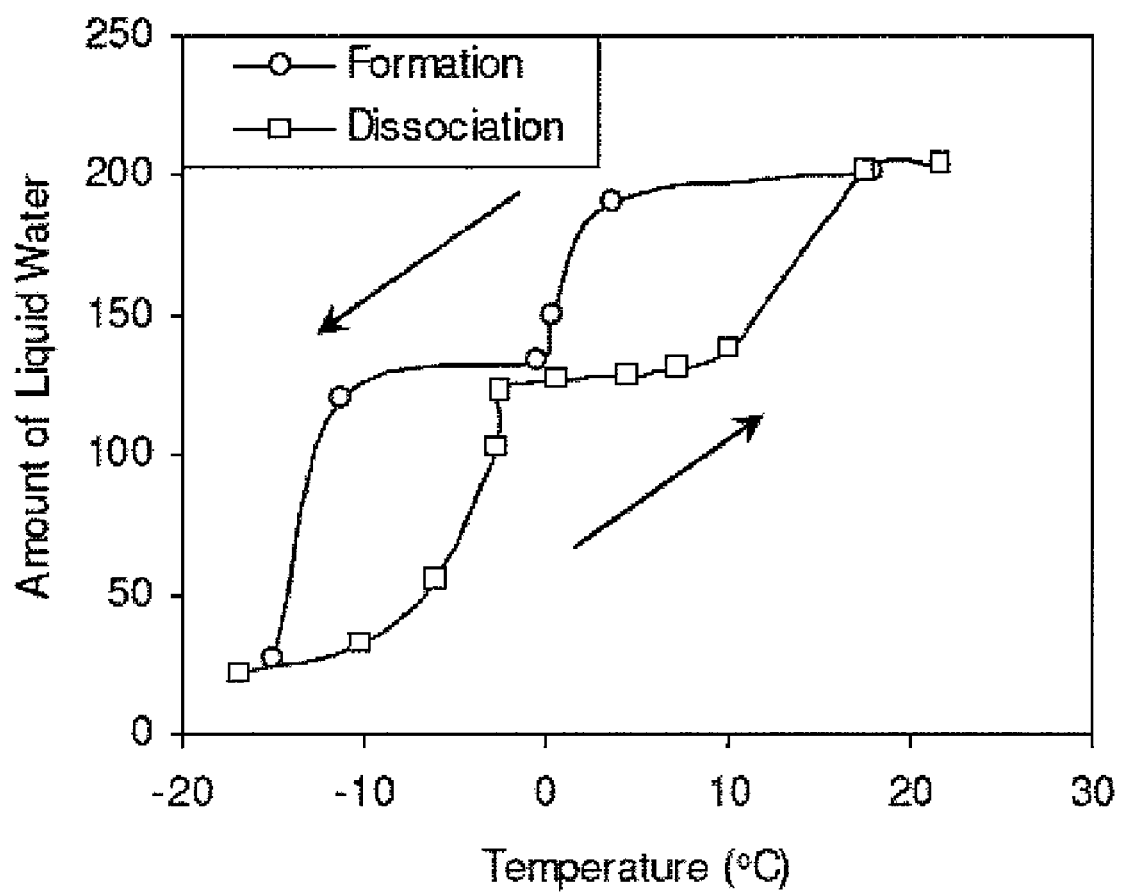
FIG. 4 is a plot of the amount of liquid water as a function of temperature during hydrate formation and dissociation in black oil at 2000 psi.

As shown in FIG. 4, which is a plot of the amount of liquid water in the sample as a function of temperature during hydrate formation and dissociation, hydrate onset was detected by a decrease in water peak area around 2° C.-3° C. As discussed hereinabove, the hydrate onset in the emulsion did not cause large-scale hydrate formation. A large amount of water remained in liquid state after initial hydrate formation. Further cooling had no effect on the liquid water content until around −15° C., at which temperature another drop occurred. About 10% of water remained in the liquid state even at −17° C. This second disappearance of liquid water was probably due to the formation of ice. Support for this conjecture was found when, upon warming, dissociation occurred over a wide range of temperatures before the temperature reached zero. Ice formation/melting temperatures in water/oil emulsions are subject to Rayleigh depressions and are dependent on droplet sizes. The melting temperature of ice crystallites in an emulsion would be expected to span some range related to the droplet size distribution. The amount of hydrate formation at subzero temperatures can be calculated from the difference between the formation and dissociation curves around −1° C. Subsequently, the amount of ice formation can be estimated by the total disappearance of liquid water at subzero temperatures deducted by the amount of hydrate formation at these temperatures. Dissociation reached a plateau after 0° C. and no further dissociation occurred until around 14° C. Total dissociation of hydrate occurred around 17° C. and the water peak area returned to the original value.

The hydrate was assumed to be structure I methane hydrate. However, it is possible that other components of petroleum, such as methylcyclopentane, methylcyclohexane, neohexane, and adamantine, which can form some structure H hydrate with the help of methane were formed. It is to be noted that the current method is indifferent to the specific type of hydrate structures involved when disappearance of water is used to indicate precipitant formation.

Example 2

THF Relaxometry

The system of THF and water, that form structure II hydrate at ~4.5° C. under ambient pressure, was selected to study clathrate hydrate mechanisms because formation conditions are mild and THF is miscible with water at conditions of interest. Hydrate formation and dissociation were studied by measuring $T_2$ of THF in $D_2O$. Low-field NMR spin-spin relaxation time ($T_2$) distributions were employed to investigate THF clathrate hydrate formation and dissociation in deuterium oxide ($D_2O$). It was found that $T_2$ measurements easily distinguish THF in a solid hydrate phase from THF in the coexisting liquid phase.

Figure 5:
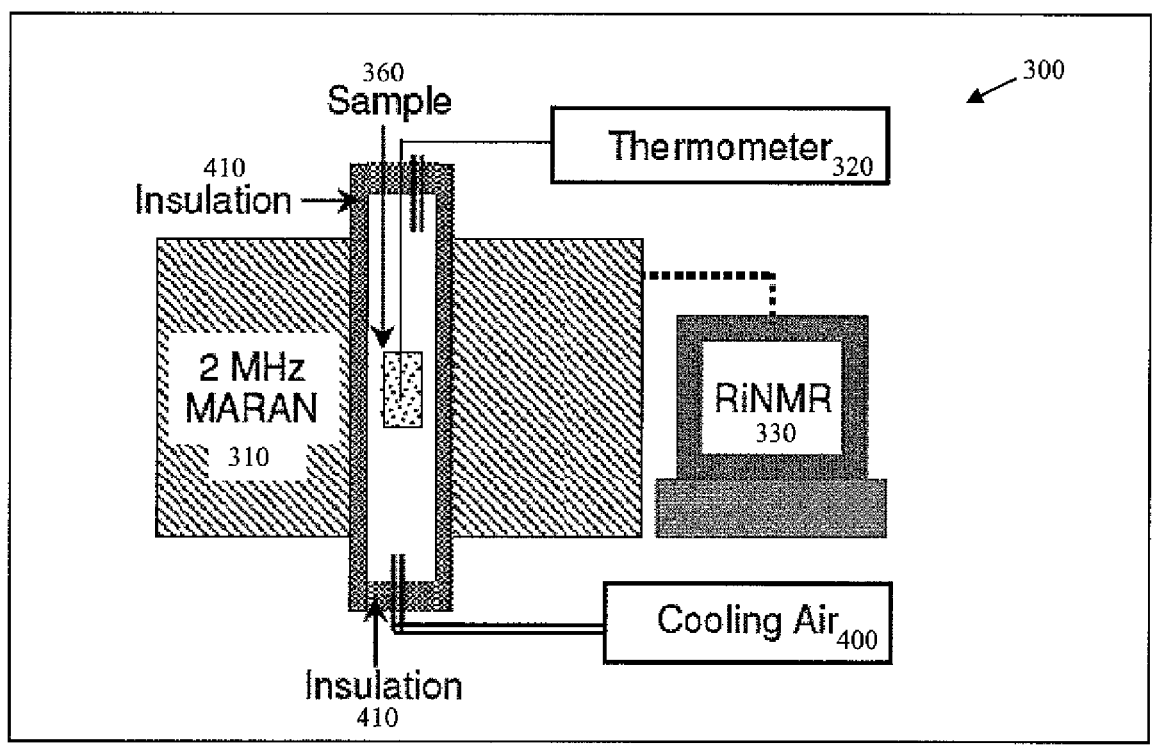
FIG. 5 is a schematic of a setup for performing $T_2$ relaxometry on a hydrocarbon stream.

A schematic of an experimental setup to detect the presence of precipitant with NMR relaxometry 300 is shown in FIG. 5. $T_2$ distribution measurements of the protons in THF (Aldrich, 99+%) in $D_2O$ (Cambridge Isotope Laboratories, D 99.9%) were obtained with a 2 MHz RI Maran NMR spectrometer 310 using Carr-Purcell-Mieboom-Gill (CPMG) technique as known to those of skill in the art. The instrument has a dead time of 60 µs. In the CPMG pulse sequence, the 90-180 degree pulse gap is 166.7 µs. Data were acquired by RiNMR software 330 and processed using WinDXP program.

The temperature of spectrometer 310 should be maintained at 30° C. to maintain stability of the system's permanent magnet. Thermal insulation 410 was therefore placed along the inside surface of the sample bore as an Air-Jet temperature controller supplied dry air 400 to control temperature of sample 360. The controller is capable of providing air temperature from −40° C. to 100° C. with 0.1° C. stability. A glass bottle with a cap having a Teflon liner was used to contain 20 mL of the THF-$D_2O$ solution (molar ratio 1:17) and was tightly sealed to prevent THF evaporating into the environment. Sample 360 was weighed and no THF loss was detected after two weeks. A LUXTRON fluoroptic thermometer 320 was mounted into the glass container through the cap to monitor the sample temperature with a resolution of 0.1° C.

Since trace amounts of oxygen may alter $T_2$ of THF significantly, pure $D_2O$ and THF liquids were deoxygenated separately in a closed glovebox with nitrogen environment. $D_2O$ and THF were contained in two separate Teflon bottles. The gas phase above the liquid phase was periodically flushed with nitrogen gas and the bottles were periodically shaken to facilitate the diffusion of oxygen out of the liquid phase. After the gas phase had been flushed six or seven times for about 12 hours, THF and $D_2O$ were mixed on the molar basis of 1:17 in the glass bottle. This is the same concentration of THF as in the hydrate phase. Therefore, as hydrate forms, the liquid phase composition should not change. Sample 360 was then sealed and moved into the Maran spectrometer 310 for measurements. It was carefully placed in the "sweet" spot of the magnet, the location where the magnetic field is most homogeneous.

To ensure that the THF-$D_2O$ solution was homogeneous and in its equilibrium configuration before hydrate formation, in this study, the freshly mixed THF-$D_2O$ solution was first turned into hydrate and subsequently dissociated. It was warmed to 35° C. for about two hours to eliminate any possible remnant hydrogen bonding structure. $T_2$ measurements were started as the sample was cooled in steps until the point of hydrate nucleation, which is identified by the sudden rise of the sample temperature. The temperature of the cooling air was then adjusted to slow the hydrate formation rate for better $T_2$ measurements. After each measurement, WinDXP program was run to calculate the $T_2$ distribution. A single measurement took about 5-10 minutes to complete, depending upon the number of scans and the delay time between two consecutive scans. After complete hydrate formation, marked by the disappearance of the THF liquid peak in the $T_2$ distribution, the sample was further cooled to measure the $T_2$ behavior in THF hydrate with regard to the temperature. The sample was then warmed to slowly dissociate the hydrate and the temperature was then raised to room temperature in increments.

Figure 6:
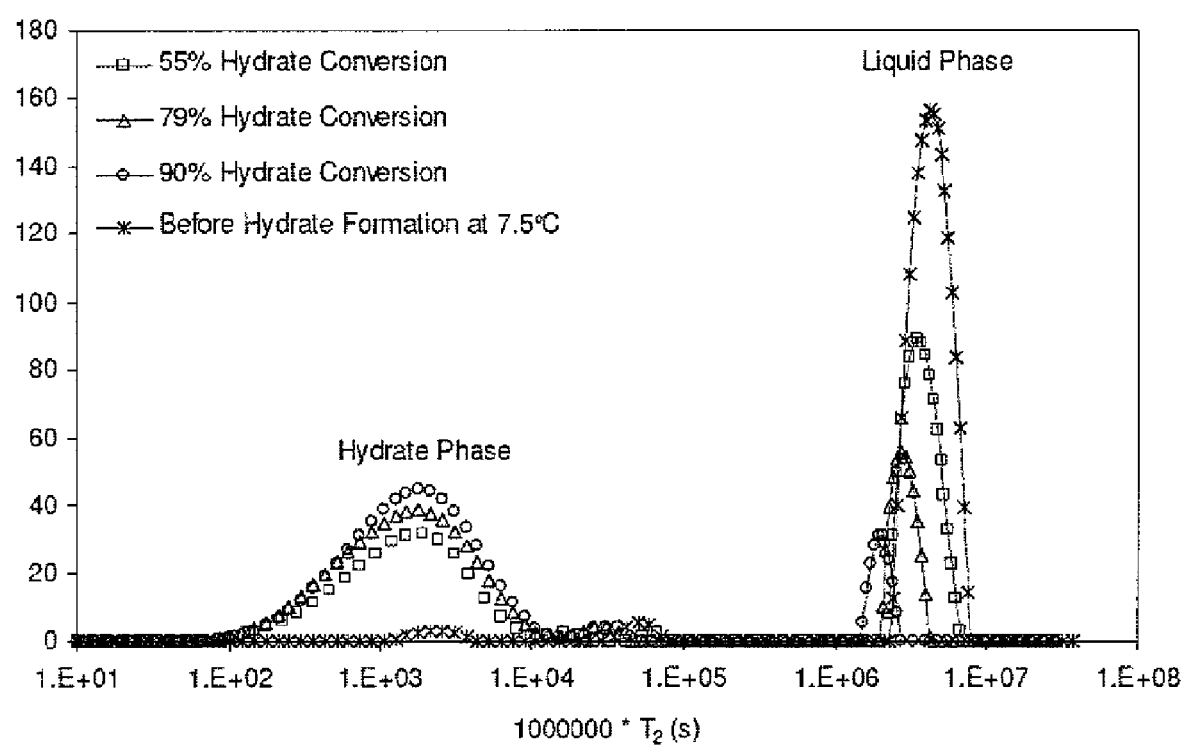
FIG. 6 shows $T_2$ distributions of THF in $D_2O$ at different hydrate conversion percentages during hydrate formation, compared with the $T_2$ distribution of THF in $D_2O$ before hydrate formation at the hydrate equilibrium temperature.
Figure 7:
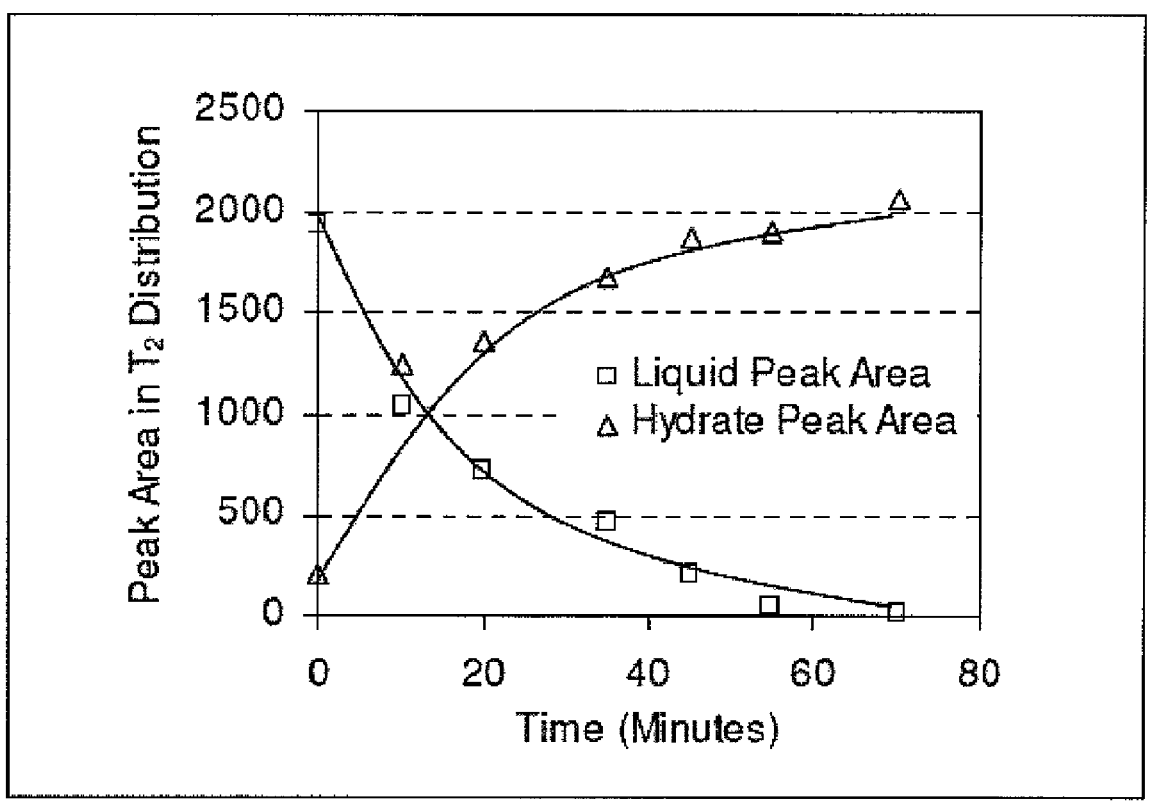
FIG. 7 is a plot of peak area of $T_2$ distribution of THF in liquid phase and hydrate phase during hydrate formation as a function of time.

$T_2$ distributions of THF in $D_2O$ during hydrate formation are presented in FIG. 6, along with the $T_2$ distribution before hydrate formation at 7.5° C., which is close to the THF/$D_2O$ hydrate equilibrium temperature of ~7.4° C. that was measured in this work. The THF in the hydrate phase and the coexisting liquid phase are easily separated into two distinguishable peaks. $T_2$ of THF in hydrate phase was ~2-3 ms, while the $T_2$ of THF in liquid phase changed from 4.2 s to 3.5 s to 2 s as the percentage of hydrate in the sample increased from 0% to 55% to 90%. Relaxometry parameters for THF in $D_2O$ depend significantly on the phase fraction when the liquid coexisting with hydrate phase at the THF/$D_2O$ hydrate equilibrium temperature, which is ~7.4° C. as found herein. $T_2$ decreased as more liquid phase was converted into hydrate. FIG. 7 is a plot of peak area of $T_2$ distribution of THF in liquid phase and hydrate phase during hydrate formation as a function of time. As shown in FIG. 7, during hydrate formation, hydrate peak area increased while the liquid peak area decreased, and the sum of hydrate and liquid peak areas was conserved within about ±5%. The conservation of total peak area indicates that, during the transition, THF molecules inhabit two distinct states. Lines are added for ease of viewing.

Example 3

Asphaltene and Paraffin Relaxometry

Asphaltene agglomeration and flocculation were studied by measuring the $T_2$ distributions of black oils subjected to $CO_2$ injection at low pressures. Low-field NMR spin-spin relaxation time ($T_2$) distributions were employed to investigate the change in the $T_2$ distribution as a function of the exposure time of the oil to $CO_2$. $T_2$ measurements clearly demonstrated the agglomeration of large molecular species in black oil as a result of $CO_2$ exposure.

A schematic of the experimental setup 300 used to perform $T_2$ distribution measurements of the protons in black oil is shown in FIG. 5. $T_2$ distribution measurements were obtained with a 2 MHz RI Maran NMR spectrometer 310 using Carr-Purcell-Mieboom-Gill (CPMG) technique as known to those of skill in the art. The instrument has a dead time of 60 μs. In the CPMG pulse sequence, the 90-180 degree pulse gap is 166.7 μs. Data were acquired by RiNMR software 330 and processed using WinDXP program. The temperature of spectrometer 310 should be maintained at 30° C. to maintain stability of the system's permanent magnet.

Since trace amounts of oxygen may alter $T_2$ of oil, samples were deoxygenated in a closed glovebox with nitrogen environment. The gas phase above the oil liquid phase was periodically flushed with nitrogen gas and the containers periodically shaken to facilitate the diffusion of oxygen out of the liquid phase. After the gas phase had been flushed six or seven times for about 12 hours, the oil was placed in a closed low pressure container and moved into the Maran spectrometer 310 for measurements. It was carefully placed in the "sweet" spot of the magnet, the location where the magnetic field is most homogeneous.

Injection of $CO_2$ was accomplished by bubbling gas through the sample with a 140 psig backpressure. After each measurement, WinDXP program was run to calculate the $T_2$ distribution. A single measurement took about 5-10 minutes to complete, depending upon the number of scans and the delay time between two consecutive scans. Measurements were taken over a number of hours to determine the temporal effect of $CO_2$ on asphaltene agglomeration.

Figure 8:
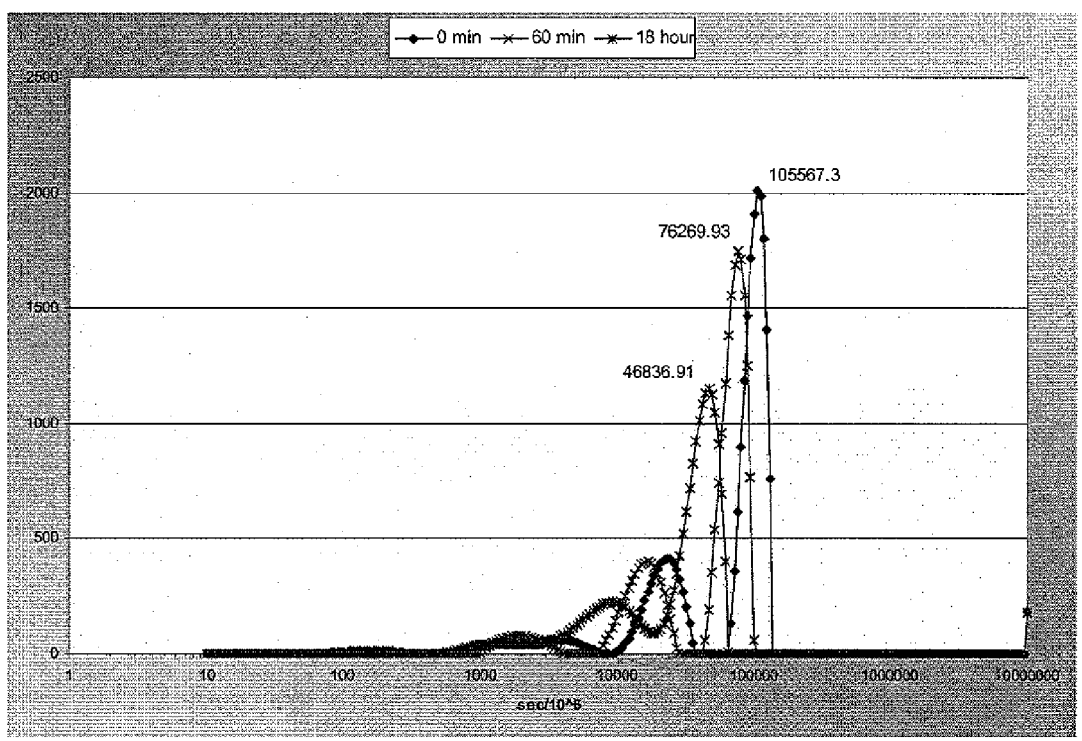
FIG. 8 shows $T_2$ distributions of oil as a function of $CO_2$ injection time.

$T_2$ distributions of the oil as a function of $CO_2$ injection time are presented in FIG. 8. The low $T_2$ values generally correspond to large molecules while the high values correspond to the smaller molecules in the oil. As large molecules agglomerate into larger ones, their relaxation times decrease resulting in a shift downward in the $T_2$ distribution.

As shown in FIG. 8, $CO_2$ injection over time induces a lowering of the relaxation time of the larger species indicating potential asphaltene agglomeration.

To confirm the application, black oil samples known to be comprised of asphaltene and only light hydrocarbons were studied as above. Such systems exhibit a bimodal distribution. The asphaltene and solvent molecules are so different in size that their relaxation times do not overlap so their response to $CO_2$ can be individually assessed.

Figure 9:
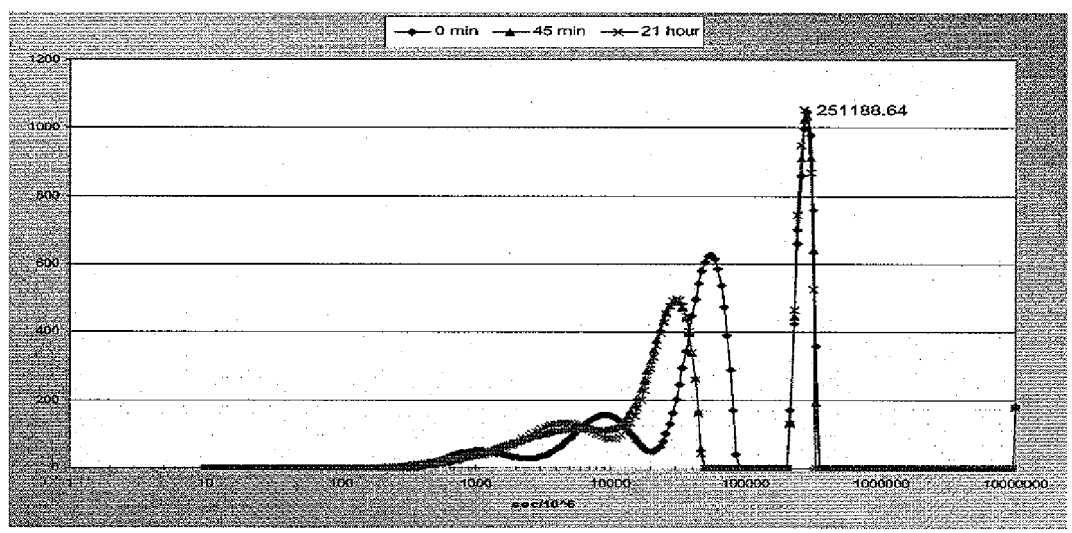
FIG. 9 shows $T_2$ distributions of the asphaltene/light hydrocarbon samples as a function of time.

FIG. 9 shows the $T_2$ distributions of the asphaltene/light hydrocarbon samples as a function of time. No reduction is observed in the $T_2$ values of the light hydrocarbons. However, the $T_2$ of heavy asphaltenes decreases dramatically with $CO_2$ exposure.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference in the Description of Related Art is not an admission that it is prior art to the present invention, especially any reference that may have a publication date after the priority date of this application. The disclosures of all patents, patent applications, and publications cited herein are hereby incorporated by reference, to the extent that they provide exemplary, procedural or other details supplementary to those set forth herein.

The invention claimed is:

1. A method for detecting the presence of precipitants in a hydrocarbon stream, the method comprising:
   introducing at least a portion of the hydrocarbon stream into a measurement chamber of an NMR measuring device;
   assaying the fluids in the chamber with proton nuclear magnetic resonance to obtain NMR signals;
   processing the NMR signals; and
   detecting the formation of precipitants in the hydrocarbon stream based on the processing.

2. The method of claim 1 wherein assaying the fluids in the chamber with proton nuclear magnetic resonance to obtain NMR signals comprises performing NMR spectroscopy or NMR relaxometry, and wherein processing the NMR signals comprises monitoring the NMR signals to detect changes in the liquid water content over time which can be correlated with hydrate formation.

3. The method of claim 2 wherein the NMR measuring device is connected with a transport pipeline.

4. The method of claim 3 wherein introducing at least a portion of the hydrocarbon stream into a measurement chamber of an NMR measuring device comprises pulling a slipstream from the transport pipeline.

5. The method of claim 2 wherein the monitoring of the NMR signals to detect changes in the liquid water content occurs substantially in real time.

6. The method of claim 2 wherein assaying the fluids in the chamber with proton nuclear magnetic resonance to obtain NMR signals comprises performing NMR spectroscopy, and wherein monitoring the NMR signals to detect changes in liquid water content comprises monitoring the liquid water peaks of the measured frequency spectra.

7. The method of claim 2 further comprising determining a baseline NMR liquid water signal for the hydrocarbon stream and defining an operating range having a low NMR liquid water signal and a high NMR liquid water signal and signaling a response if a subsequently measured NMR liquid water signal falls outside the predetermined operating range.

8. The method of claim 2 wherein performing NMR relaxometry comprises measuring a baseline $T_2$ relaxation distribution of the hydrocarbon stream and subsequently measuring the $T_2$ relaxation distribution of the hydrocarbon stream over time, and wherein processing the NMR signals obtained to detect the formation of precipitants in the hydrocarbon stream comprises monitoring subsequently measured $T_2$ distributions of the hydrocarbon stream to detect a shift in the $T_2$ distribution from baseline indicating the formation of solid precipitant.

9. The method of claim 8 wherein the precipitant is selected from the group consisting of hydrates, asphaltenes, paraffins, and combinations thereof.

10. A method of analyzing a hydrocarbon stream comprising:
    carrying out the method of claim 1 at a first location;
    carrying out the method of claim 1 at a second location downstream of the first location; and
    comparing the NMR signals obtained at each location to detect precipitation of precipitant between the two locations.

11. The method of claim 10 wherein comparing the NMR signals obtained at each location to detect precipitation of precipitant between the two locations comprises monitoring relaxation distribution, frequency spectra, or both at the first and second locations and comparing the relaxation distribution, frequency spectra, or both at the first and second locations to detect changes in the liquid water content of the hydrocarbon stream and correlating changes in liquid water content with precipitant formation.

12. The method of claim 11 wherein the change in liquid water content is correlated with hydrate formation.

13. The method of claim 10 wherein assaying the fluids in the chamber with proton nuclear magnetic resonance comprises performing NMR relaxometry to determine the $T_2$ relaxation distribution, the method further comprising measuring a baseline $T_2$ relaxation distribution and correlating a shift of subsequently measured $T_2$ relaxation distribution from the baseline $T_2$ relaxation distribution with precipitant formation.

14. The method of claim 13 further comprising calculating the areas under the $T_2$ relaxation distribution curves to determine amount of precipitant precipitated.

15. The method of claim 13 wherein the precipitant is selected from the group consisting of paraffins, asphaltenes, hydrates, and combinations thereof.

16. The method of claim 10 wherein the first and second locations are locations along a transport pipeline.

17. A method for determining the hydrate thermodynamic point of a hydrocarbon stream comprising:
    carrying out the method of claim 1 over a range of temperatures to determine the hydrate thermodynamic point of the hydrocarbon stream, wherein assaying the fluids in the chamber with proton nuclear magnetic resonance comprises performing NMR spectroscopy; the method further comprising determining the amount of hydrate present at each temperature from the liquid water peaks of the NMR frequency spectra and determining the hydrate thermodynamic point of the hydrocarbon stream as the temperature at which the last hydrate crystal dissociates.

18. A method of monitoring the liquid water content of a hydrocarbon stream in a flowline comprising:
    introducing at least a portion of the hydrocarbon stream into an NMR measuring device;
    measuring a baseline NMR liquid water signal of the hydrocarbon stream; and
    comparing subsequent NMR liquid water signals with the baseline NMR liquid water signal to detect changes in the liquid water content of the hydrocarbon stream.

19. The method of claim 18 further comprising signaling a response if the water content of the hydrocarbon stream changes by more than 5% from the baseline water content.

20. The method of claim 18 wherein monitoring of the NMR signals to detect changes in the liquid water content occurs substantially in real time.

* * * * *